(12) United States Patent
Fitzpatrick et al.

(10) Patent No.: US 10,843,951 B2
(45) Date of Patent: Nov. 24, 2020

(54) SEA WATER HARVESTING PROCESS

(71) Applicant: ORIEL SEASALT COMPANY LIMITED, Killester (IE)

(72) Inventors: Brian Fitzpatrick, Dublin (IE); John Delany, Laytown (IE)

(73) Assignee: Oriel Seasalt Company Limited, Dublin (IE)

( * ) Notice: Subject to any disclaimer, the term of this patent is extended or adjusted under 35 U.S.C. 154(b) by 0 days.

(21) Appl. No.: 15/105,797

(22) PCT Filed: Dec. 19, 2014

(86) PCT No.: PCT/EP2014/078878
§ 371 (c)(1),
(2) Date: Jun. 17, 2016

(87) PCT Pub. No.: WO2015/092025
PCT Pub. Date: Jun. 25, 2015

(65) Prior Publication Data
US 2016/0318784 A1     Nov. 3, 2016

(30) Foreign Application Priority Data

Dec. 20, 2013   (IE) .................................. S2013/0385

(51) Int. Cl.
*C02F 9/00*      (2006.01)
*C02F 1/38*      (2006.01)
(Continued)

(52) U.S. Cl.
CPC .................. *C02F 9/00* (2013.01); *A61K 8/20* (2013.01); *A61K 33/14* (2013.01); *A61Q 19/00* (2013.01);
(Continued)

(58) Field of Classification Search
None
See application file for complete search history.

(56) References Cited

U.S. PATENT DOCUMENTS 2,054,624 A * 9/1936 Griffith .................. A23B 4/023
159/47.1
3,647,396 A * 3/1972 DeWittie ................. C01D 3/22
209/5
(Continued)

FOREIGN PATENT DOCUMENTS

| CN | 101367538 A | * | 2/2009 |
| GB | 2395946 A | | 6/2004 |
| JP | 2003212537 A | | 7/2003 |

OTHER PUBLICATIONS

Thibault, V., International Application No. PCT/EP2014/078878, International Search Report and Written Opinion, dated Apr. 9, 2015, 12 pages.
(Continued)

*Primary Examiner* — Krishnan S Menon
(74) *Attorney, Agent, or Firm* — LaBatt, LLC

(57) ABSTRACT

A sea water harvesting process includes the steps of collecting sea water, filtering the sea water, passing the filtered sea water through a high-pressure reverse osmosis membrane to separate the sea water into de-salinated water and concentrated sea water, delivering the concentrated sea water to an evaporator, heating the concentrated sea water in the evaporator under vacuum to produce calcium sulphate, sea salt and a super-concentrated sea water. Downstream of the evaporator the super-concentrated sea water is heated to produce a concentrated mineral liquor containing sea minerals in a concentration of about 42%.

10 Claims, 3 Drawing Sheets

(51) Int. Cl.
| | |
|---|---|
| *C02F 1/44* | (2006.01) |
| *C02F 1/467* | (2006.01) |
| *C02F 1/68* | (2006.01) |
| *B01D 1/18* | (2006.01) |
| *C02F 1/00* | (2006.01) |
| *C01D 3/06* | (2006.01) |
| *C01F 11/46* | (2006.01) |
| *A61K 8/20* | (2006.01) |
| *A61K 33/14* | (2006.01) |
| *A61Q 19/00* | (2006.01) |
| *C02F 1/06* | (2006.01) |
| *C25B 1/34* | (2006.01) |
| *C02F 103/02* | (2006.01) |
| *C02F 103/08* | (2006.01) |
| *C02F 1/04* | (2006.01) |

(52) U.S. Cl.
CPC ............... *B01D 1/18* (2013.01); *C01D 3/06* (2013.01); *C01F 11/46* (2013.01); *C02F 1/001* (2013.01); *C02F 1/06* (2013.01); *C02F 1/385* (2013.01); *C02F 1/441* (2013.01); *C02F 1/444* (2013.01); *C02F 1/4672* (2013.01); *C02F 1/68* (2013.01); *C25B 1/34* (2013.01); *A61K 2800/10* (2013.01); *C02F 1/04* (2013.01); *C02F 2103/026* (2013.01); *C02F 2103/08* (2013.01); *C02F 2301/063* (2013.01); *Y02A 20/128* (2018.01); *Y02A 20/131* (2018.01)

(56) References Cited

U.S. PATENT DOCUMENTS

| | | |
|---|---|---|
| 5,238,574 A | 8/1993 | Kawashima et al. |
| 6,783,682 B1 | 8/2004 | Awerbuch |
| 2005/0242032 A1 | 11/2005 | Sugito et al. |
| 2012/0160753 A1 | 6/2012 | Vora et al. |
| 2013/0112571 A1* | 5/2013 | Doi .................. C02F 1/4674 205/498 |

OTHER PUBLICATIONS

Examination Report for EP Application No. 14828154.6, dated Apr. 25, 2017, 6 pages.

Intention to Grant for EP Application No. 14828154.6, dated Mar. 6, 2018, 40 pages.

* cited by examiner

SEA WATER HARVESTING PROCESS

INTRODUCTION

This invention relates to a sea water harvesting process.

The invention is particularly concerned with obtaining sea salt, sea minerals and mineral water from sea water in an efficient manner.

SUMMARY OF THE INVENTION

According to the invention there is provided a sea water harvesting process including the steps of collecting sea water, filtering the sea water, passing the filtered sea water through a high-pressure reverse osmosis membrane to separate the sea water into de-salinated water and concentrated sea water, delivering the concentrated sea water to an evaporator, heating the concentrated sea water in the evaporator under vacuum to produce calcium sulphate, sea salt and a super-concentrated sea water from which concentrated sea minerals are derived.

In one embodiment of the invention the sea water harvesting process includes the steps:

delivering sea water through a filtering system and then through a reverse osmosis system for separating the sea water into concentrated sea water having a density of 5%-10% and de-salinated water, delivering concentrated sea water to an evaporator, heating the concentrated sea water under vacuum in the evaporator to produce a super-concentrated sea water having a density in the range 23% to 27%, and discharging super-concentrated sea water from the evaporator and further heating the super-concentrated sea water under pressure to produce a concentrated sea minerals liquor containing sea minerals in a concentration in the range 37%-47%.

In a preferred embodiment the process includes delivering the sea salt in the form of a slurry comprising a mixture of sea salt and super-concentrated sea water from the evaporator to a centrifuge and separating sea salt from the super-concentrated sea water in the centrifuge.

Optionally, sea salt discharged from the centrifuge may be delivered to a roaster and the process includes flash roasting the sea salt.

In one embodiment, the process includes delivering super-concentrated sea water having a density in the range 23% to 27% from the evaporator to a super-concentrated sea water tank.

In a further embodiment, the process includes delivering super-concentrated sea water discharged from the centrifuge to the super-concentrated sea water tank.

In another embodiment, the process includes delivering a calcium sulphate and super-concentrated sea water mixture from the evaporator to a calcium settling device and separating the calcium sulphate from the super-concentrated sea water in the calcium settling device.

In another embodiment, the process includes delivering super-concentrated sea water separated from the calcium sulphate to the super-concentrated sea water tank.

In another embodiment, the process includes washing the calcium sulphate by adding fresh water to the calcium sulphate, allowing the calcium sulphate and fresh water to separate and then removing the separated water.

In another embodiment, the process includes carrying out the washing step at least twice.

In a further embodiment the process includes delivering super-concentrated sea water from the evaporator to a concentrated sea mineral capsule, subjecting the super-concentrated sea water to a temperature in excess of 100° C. for separating additional salt from the super-concentrated sea water leaving the concentrated sea minerals liquor.

In another embodiment the process includes separating flake salt from the concentrated sea minerals liquor in the concentrated sea minerals capsule.

In another embodiment the process includes recycling super-concentrated sea water from the concentrated sea mineral capsule to the super-concentrated sea water storage tank.

In another embodiment the process includes delivering the de-salinated water through a low pressure reverse osmosis system and collecting the de-salinated water discharged from the low pressure reverse osmosis system in a water storage tank.

In another embodiment, the process includes adding selected minerals in pre-desired concentrations to the de-salinated water to provide potable mineral water. This advantageously allows control of the level and type of minerals to be used.

In another embodiment the process includes downstream of the low pressure reverse osmosis system adding salt to the water and passing re-salinated water over an electric charge element for producing electrolysed oxidised water.

In another embodiment the electrolysed oxidised water has an oxidising reduction potential in the range 900-1200 mV.

In another aspect the invention provides a concentrated sea minerals product as described herein.

BRIEF DESCRIPTION OF THE DRAWINGS

The invention will be more clearly understood by the following description of some embodiments thereof, given by way of example only with reference to the accompanying drawings, in which.

DETAILED DESCRIPTION OF THE PREFERRED EMBODIMENTS

Figure 1:
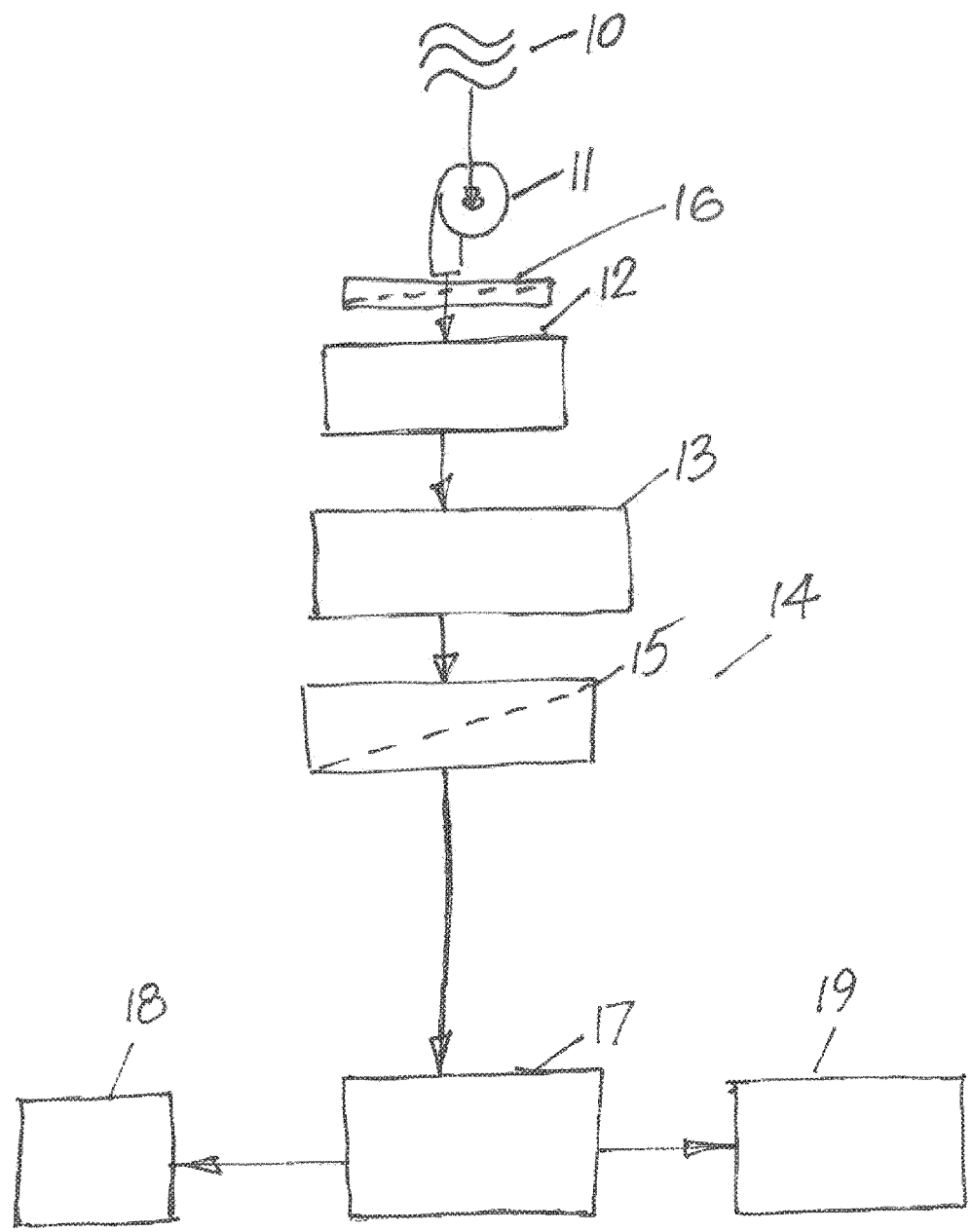
FIG. 1 is a schematic illustration of portion of a sea water harvesting process according to the invention.
Figure 2:
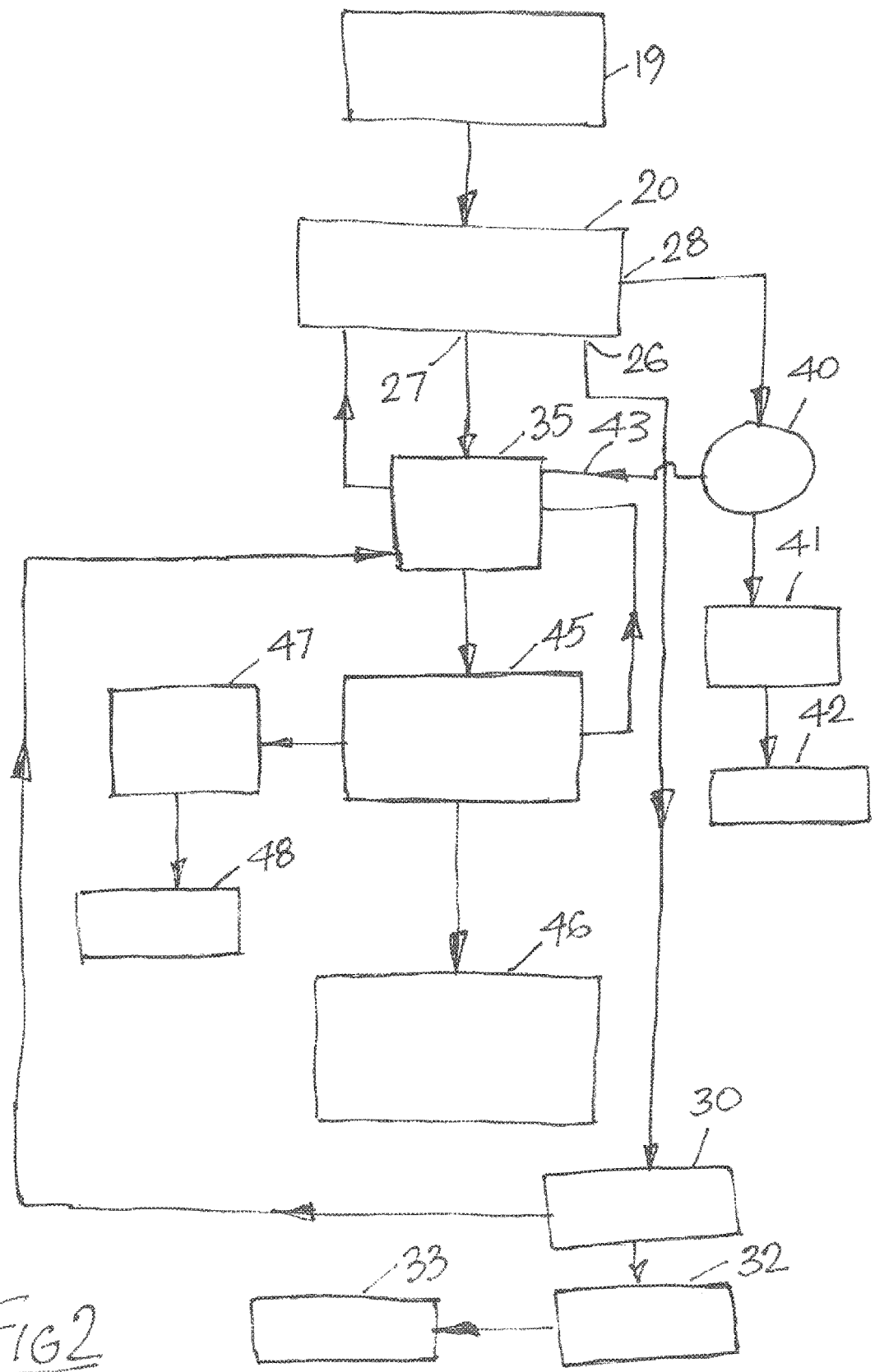
FIG. 2 is a schematic illustration of portion of the sea water harvesting process.

Referring to the drawings a process according to the invention will now be described.

Sea water 10 is pumped from the sea by a submersible pump 11 through a filtration system 16 into one or more raw sea water storage tanks 12 wherein it is allowed to settle.

The sea water is then pumped from a sea water storage tank 12 into a pre-treatment tank 13 and from there it is filtered and pumped at a pressure of about 900 psi (60 bar) to a high pressure reverse osmosis system indicated generally by the reference numeral 14. In passing through the high pressure reverse osmosis system 14 the raw sea water is separated into de-salinated water which is collected in an interval tank 18 and concentrated sea water which is collected in a concentrated sea water tank 19. The concentrated sea water is concentrated by approximately 100% to a density of approximately 6-7% i.e. having a salt/mineral content of approximately 6-7%.

From the reverse osmosis system 14 there are two outputs, namely for concentrated sea water and de-salinated sea water.

1. Concentrated Sea Water (Approximate Density 6-7%)

The processing of the concentrated sea water is as follows. The raw sea water is pumped from the pre-treatment tank 13 to an ultra-filtration (UF) membrane 15 (which is located within the reverse osmosis system 14). From the UF membrane 15 the sea water is pumped to high pressure reverse osmosis membranes 17. In passing through the high pressure reverse osmosis membranes 17 the sea water is separated into de-salinated water and concentrated sea water. De-salinated water is collected in the interval tank 18. The concentrated sea water is sent to the concentrated sea water storage tank 19. From here it is pumped as required to an evaporator 20, described later.

Figure 3:
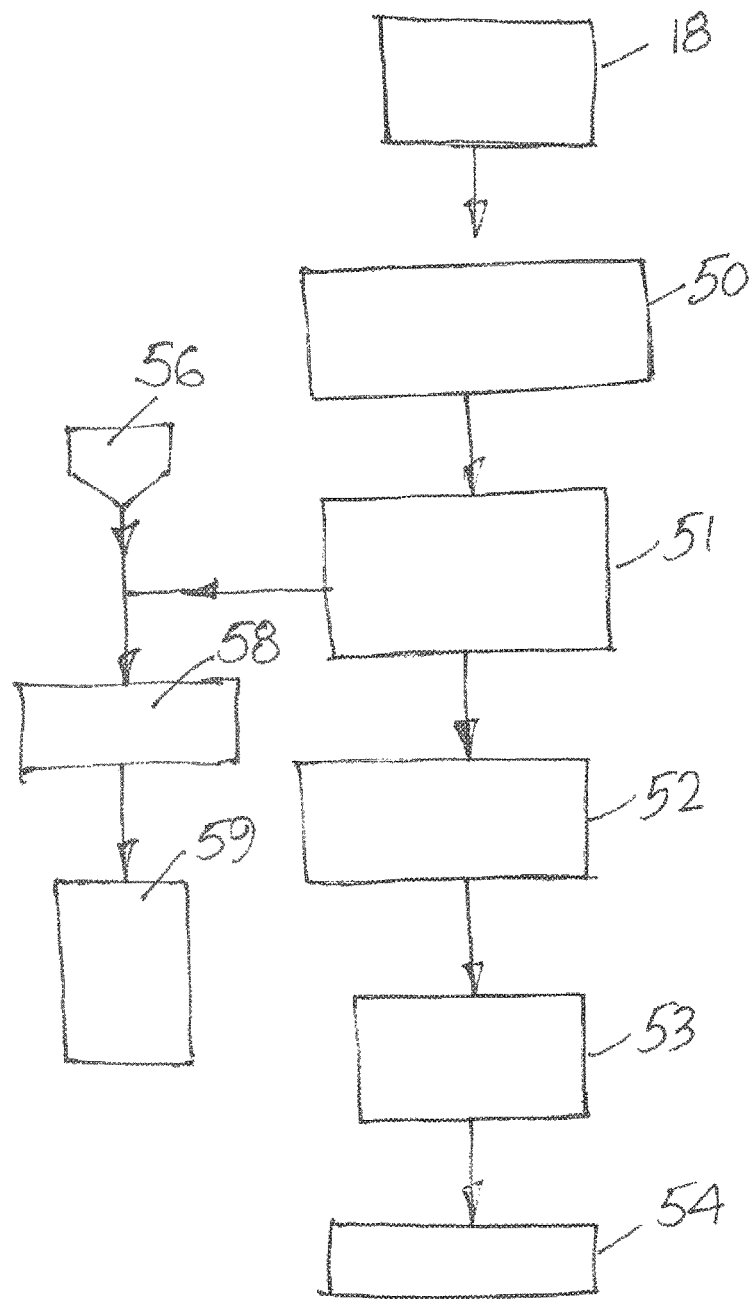
FIG. 3 is a schematic illustration of a further portion of the sea water harvesting process.

2. De-Salinated Water. The de-salinated water is pumped from the high pressure reverse osmosis membranes 17 into the interval tank 18. From the interval tank 18 it is ready to go through a low pressure reverse osmosis system 50 (FIG. 3). Once it passes through the low pressure reverse osmosis system 50 it is pumped into a stainless steel water storage tank 51 (FIG. 3) as it is now suitable for drinking. However it is not yet "Mineral Water" as minerals have to be added in later as described below.

Some of the water from the water storage tank 51 may be used in the production of electrolysed oxidised water (EO water). This is achieved by delivering water from the water storage tank 51, adding a small volume of salt 56 back into the water and then passing the re-salinated water over an electric charge element 58 for producing EO water 59. The electric charge element 58 electrically charges the re-salinated water to an oxidising reduction potential (ORP) in the range 900-1200 mV.

Evaporator

A batch of concentrated sea water (6-7%) is pumped into the evaporator 20 from the concentrated sea water tank 19. Once the concentrated sea water enters the evaporator 20 it is subjected to a temperature in the range of 55-65° C., preferably about 60° C., and to a vacuum pressure of about 0.8 bar (Gauge value). This results in the separation of the sea water over a period of 12-24 hours in the following manner.

From the evaporator 20 there are three outputs, namely a calcium sulphate outlet 26, a super-concentrated sea water outlet 27 and a sea salt outlet 28.

1. Calcium Sulphate: The first part of the output from the evaporator process is calcium sulphate. This is pumped to a calcium settling device 30 in the form of a mixture of calcium sulphate and super-concentrated sea water to allow it to flow at a density of approximately 25%. In the calcium settling device 30 calcium sulphate is separated from the super-concentrated sea water.

After separation in the calcium settling device 30, the super-concentrated sea water is moved to a super-concentrated sea water tank 35.

The remaining calcium sulphate is now in a thick white semi solid/semi liquid and it is released out through a release valve at the base of the calcium settling device 30 into a separate container 32.

When the calcium sulphate is left to settle it will become almost solid like with a clear liquid on top of it. This clear liquid is super-concentrated sea water. However when this solution is agitated and stirred it becomes slurry like. The calcium sulphate is now approximately 50% calcium sulphate and 50% super-concentrated sea water.

2. Super-Concentrated Sea Water

This is now concentrated at approximately 23%-27% density and it represents about 75% of the total contents (salt and super-concentrated sea water) of the evaporator 20 after extraction of calcium sulphate.

3. Sea Salt

This is now in a form of slurry which will leave the evaporator 20 as a mix of salt and super-concentrated sea water. It represents approximately 50% of the total contents of the evaporator 20 (the total contents inside evaporator 20 is now salt and super-concentrated sea water).

This slurry is pumped to a centrifuge 40. As the slurry is processed through the centrifuge 40 the super-concentrated sea water is removed. The salt leaves the centrifuge 40 as a powder salt 41 which is now ready for a roaster 42.

Centrifuge

The centrifuge 40 is used to separate the sea salt and the super-concentrated sea water which has been pumped from the evaporator 20. It does this through a rapid turning of the interior barrels which causes the super-concentrated sea water to separate and the sea salt to be forced against the outer casing and then extracted. The sea salt extracted from the centrifuge 40 is in a powder form (damp particles). It is now ready to use as a natural fine grain sea salt or it can be further dried through the roaster 42. The super concentrated sea water discharged from the centrifuge may be delivered to the super concentrated sea water tank 35 via return line 43.

Super-Concentrated Sea Water (Approximate Density 25%)

The super-concentrated sea water from the super-concentrated sea water tank 35 is used in two ways:
1. As the feed source for a concentrated sea minerals capsule 45 when making concentrated sea minerals.
2. As a feed source for the evaporator 20 to dilute (this is to adjust salt production volume) the mix to facilitate the effectiveness of the overall process and outputs from the evaporator 20.

Concentrated Sea Minerals

The concentrated sea minerals liquor is produced in the concentrated sea mineral capsule 45. The super-concentrated sea water is pumped to the concentrated sea mineral capsule 45 at a density of approximately 25% from the super-concentrated sea water tank 35. In the concentrated sea mineral capsule 45 the super-concentrated sea water is subjected to a temperature in excess of 100° C. to separate out the majority of the remaining salt in the super-concentrated sea water to produce the concentrated sea minerals liquor having a density in the range 37% to 47% depending on the required use.

Once produced the concentrated sea minerals are pumped to the concentrated sea minerals tank 46. Flake salt 47 produced as a by-product of this part of the process is also removed for packing 48.

The concentrated sea minerals are in a liquid form, as a clear or slightly brown liquor due to the mineral content.

They are rich in elemental magnesium with significant levels of elemental potassium, calcium and chloride also present. The liquor has no odour due to the extensive purification process while its texture is almost oily yet there is no oil present. It is best described as a lubricating texture that feels pleasant on the skin. Due to the fact that this concentrated blend of sea minerals contains the full spectrum of sea minerals, the human body likes it.

Sea Salt

After leaving the evaporator 20 the salt is pumped to the centrifuge 40 as a slurry mix of sea salt and super-concentrated sea water. It is then processed as follows:
Natural Sea Salt The sea salt produced through the centrifuge 40 after processing is a powder like sea salt. It has a fine grain and is very intense in its taste and strength. However it has a lower sodium level than traditional table salt. It is an ideal sea salt for the food sector as it is such a fine grain as to make it very suitable for blending as it will disperse and become soluble rapidly.
Free Flowing The natural sea salt may then be put through the roaster 42 where it is flash roasted to remove the remaining moisture while also being fused with and wrapped in the natural sea minerals. This process also has the benefit of making it a free flowing sea salt.
Flake Salt When the concentrated sea minerals are produced the flake sea salt is also produced.

Mineral Water

De-salinated water from the interval tank 18 is passed through the low pressure reverse osmosis system 50 (FIG. 3) and is collected in the stainless steel water storage tank 51. This is now fresh drinking water. However it does not contain any minerals. These minerals must now be added 52 later at a rate subject to the hardness and mineral content of the required water.

The mineral water can be stored in a potable mineral water storage tank 53 and later bottled 54 if desired.

Calcium Sulphate

The calcium sulphate is made in the calcium settling device 30. When it is ready to discharge from the calcium settling device 30 it is a mix of calcium sulphate and super-concentrated sea water.

If it is required to separate the calcium sulphate from the super-concentrated sea water then this can be done through additional processing. This can be achieved by the concentrated sea minerals capsule 45 separating the two materials. To separate the super-concentrated sea water is extracted and returned to the super-concentrated sea water tank 35.

If desired the calcium sulphate can be cleaned. In this case preferably it is washed 33 by adding fresh water to the calcium sulphate, allowing it to separate and then pouring out the separated water. This should be done at least two times.

If the calcium sulphate is not going to be used for a long period of time then it is recommended to leave it in the super-concentrated sea water.

Roaster

The powder sea salt is fed into the roaster 41 at a regular rate. This sea salt is then subjected to intense heat of 200-300° C. and is basically rapidly flash roasted in a consistent and uniform manner.

This process results in the sea salt being "coated" with the sea minerals protecting the salt from moisture absorption and allows it to be free flowing.

The sea minerals produced by the process of the invention have a number of uses. For example they may be used as an active ingredient or lubricant in all types of skincare and cosmetic products and applications to include but not exclusively, creams, gels, lotions, moisturisers, cleansers, balms, soaps, shampoos, foundations, dermatological applications, make up products, bodywash, lip balms, perfumes, aftershave and aftershave gels and lotions, suitable for male or female.

Other uses include being used as an additive/re-mineralising agent/mineral infusion additive/agent to re-mineralise purified water after the water has been purified through a reverse osmosis or other similar type of water purification process or to enhance spring, mineral or tap water, or to enhance other beverages such as juice or tea.

Other uses is as a food supplement to include as taken by drops in water or other drink, to be combined with any other substrate to form a new deep sea mineral formulation, to be put into drinks as part of a re-hydration or isotonic electrolyte replacement drink, mineral/salt recovery drink.

The sea salt produced by the process of the invention has many applications including culinary, medicinal, pharmaceutical, cosmetic and skincare applications.

The invention is not limited to the embodiments hereinbefore described which may be varied in construction and detail within the scope of the appended claims.

The invention claimed is:

1. A process for producing a concentrated sea minerals liquor from sea water including the steps:
delivering sea water through a filtering system suitable for cleaning the seawater by removal of seawater debris and then through a reverse osmosis system for separating the sea water into concentrated sea water having a concentration of 5% m/v-10% m/v and de-salinated water,
delivering the concentrated sea water to an evaporator,
heating the concentrated sea water under vacuum in the evaporator to produce a super-concentrated sea water depleted of sodium ions, chloride ions, calcium ions and sulphate ions having a concentration in the range 23% m/v to 27% m/v, a crystalized sodium chloride sea salt slurry and calcium sulphate; and
discharging the super-concentrated sea water depleted of sodium ions, chloride ions, calcium ions and sulphate ions from the evaporator and further heating the super-concentrated sea water under pressure to produce a sea minerals liquor containing sea minerals depleted of sodium ions, chloride ions, calcium ions and sulphate ions having a concentration in the range 37% m/v-47% m/v, and said sea minerals liquor being rich in magnesium ions with significant levels of potassium ions present relative to other sea minerals in said sea minerals liquor.

2. The process as claimed in claim 1 wherein the process includes delivering the crystalized sodium chloride sea salt in the form of a slurry comprising a mixture of crystalized sodium chloride sea salt and a liquid fraction comprising a portion of the super-concentrated sea water depleted of sodium ions, chloride ions, calcium ions and sulphate ions from the evaporator to a centrifuge and separating the crystalized sodium chloride sea salt from the super-concentrated sea water in the centrifuge.

3. The process as claimed in claim 1 wherein the process includes delivering super-concentrated sea water depleted of sodium ions, chloride ions, calcium ions and sulphate ions having a concentration in the range 23% m/v to 27% m/v from the evaporator to a super-concentrated sea water tank.

4. The process as claimed in claim 2 wherein the process includes delivering the liquid fraction comprising a portion of the super-concentrated sea water depleted of sodium ions, chloride ions, calcium ions and sulphate ions discharged from the centrifuge via a return line to the super-concentrated sea water tank.

5. The process as claimed in claim 1 wherein the process includes delivering a mixture of the calcium sulphate and a solvent comprising a portion of the super-concentrated sea water depleted of sodium ions, chloride ions, calcium ions and sulphate ions from the evaporator to a calcium settling device and separating the calcium sulphate from the solvent comprising a portion of the super-concentrated sea water depleted of sodium ions, chloride ions, calcium ions and sulphate ions in the calcium settling device.

6. The process as claimed in claim 5 wherein the process includes delivering the solvent comprising a portion of the super-concentrated sea water depleted of sodium ions, chloride ions, calcium ions and sulphate ions discharged from the calcium settling device to the super-concentrated sea water tank.

7. The process as claimed in claim 1 wherein the process includes delivering the super-concentrated sea water depleted of sodium ions, chloride ions, calcium ions and sulphate ions having a concentration in the range 23% m/v to 27% m/v to a concentrated sea mineral capsule, subjecting the super-concentrated sea water to a temperature in excess of 100° C. for separating additional crystalized sodium chloride flake salt from the super-concentrated sea water.

8. The process as claimed in claim 1, wherein the process includes discharging the super-concentrated sea water from the super-concentrated seawater tank and delivering the super-concentrated seawater to the concentrated sea minerals capsule.

9. The process as claimed in claim 1, wherein the process includes discharging the super-concentrated sea water from the concentrated sea minerals capsule to the super-concentrated sea water tank.

10. The process as claimed in claim 1, wherein the process includes discharging the sea minerals liquor from the concentrated sea minerals capsule to the concentrated sea mineral tank.

* * * * *